United States Patent
Keay et al.

(10) Patent No.: US 6,376,197 B1
(45) Date of Patent: Apr. 23, 2002

(54) DIAGNOSIS OF INTERSTITIAL CYSTITIS

(75) Inventors: Susan K. Keay, Ellicott City; John W. Warren, Baltimore; Michael K. Hise, Columbia, all of MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/576,396

(22) Filed: May 22, 2000

Related U.S. Application Data

(62) Division of application No. 09/109,548, filed on Jul. 2, 1998, now Pat. No. 6,156,522.
(60) Provisional application No. 60/051,458, filed on Jun. 30, 1997.

(51) Int. Cl.$^7$ ...................... G01N 33/53; G01N 33/566; C12Q 1/58; C07K 14/485
(52) U.S. Cl. .......................... 435/7.1; 435/12; 436/501; 530/350; 530/399
(58) Field of Search .................... 435/7.1, 12; 530/350, 530/399; 436/501

(56) References Cited

U.S. PATENT DOCUMENTS

| | | | |
|---|---|---|---|
| 5,811,393 A | 9/1998 | Klagsburn et al. | ............ 514/12 |
| 5,962,645 A | 10/1999 | Keay et al. | ................. 530/350 |

OTHER PUBLICATIONS

Freeman, M et al. Heparin–binding EGF–like Growth Factor is an Autocrine Growth Factor for Human Urothelial Cells and is Synthesized by Epithelial and Smooth Muscle Cells in the Human Bladder. Journal Clinical Investigation vol. 99 (5) 1028–1036 (1997).*
Hanno, P.M., et al. eds. *Interstitial cystitis*. London: Springer–Verlag (1990).
Held, P.J. et al. "Epidemiology of interstitial cystitis: 2." *Interstitial cystitis*.: 29–48. London: Springer–Verlag (1990).
Johansson, S.L. et al. "Clinical feature and spectrum of light microscopic changes in interstitial cystitis." J. Urol, 143: 1118 (1990).
Oravisto, K.J. et al. "Interstitial cystitis: Clinical and immunological findings." Scand. J. Urol. Nephrol. 4:37 (1970).
Skoluda, et al. "Kritische Bemerkungen zur Immunopathogenese der Interstitiellen Cystitis." Urologe, 13: 15 (1974).
Parsons, et al. "Epithelial dysfunction in nonbacterial cystitis (interstitial cystitis)." J. Urol 145:732 (1991).
Smith, B.H. et al. "Chronic ulcerating interstitial cystitis (Hunner's ulcer)." Arch. Path. 93:76 (1972).
Fowler J. Jr., et al. "Interstitial cystitis is associated with intraurothelial Tamm–Horsfall protein." J. Urol. 140: 1385 (1988).
Liebert, M., et al. "Evidence for urothelial cell activation in interstitial cystitis." J. Urol. 149: 470 (1993).

deBoer, W.I., et al. "Expression of growth factors and receptors during specific phases in regenerating urothelium after acute injury in vivo." Am. J. Pathol. 145: 1199 (1994).
Lynch, S.E., et al. "Growth factors in wound healing. Single and synergistic effects on partial thickness porcine wounds." J. Clin. Invest. 84: 640 (1989).
Mustoe, T.A., et al. "Growth factor–induced acceleration of tissue repair through direct and inductive activities in a rabbit dermal ulcer model." J. Clin. Invest. 87:694 (1991).
Mellin, T.N., et al. "Acidic fibroblast growth factor accelerates dermal wound healing." Growth Factors 7: 1 (1992).
Antoniades, H.N., et al. "Expression of growth factor and receptor mRNAs in skin epithelial cells following acute cutaneous injury." Am. J. Pathol. 142: 1099 (1993).
Werner, S., et al. "Large induction of keratinocyte growth factor expression in the dermis during wound healing." Proc. Natl. Acad. Sci. USA 89: 6896 (1992).
Nusrat, A., et al. "Hepatocyte growth factor/scatter factor effects on epithelia." J. Clin. Invest. 93: 2056 (1994).
Behrens, M.T., et al. "Epidermal growth factor receptor regulation in rat kidney: two models of renal growth." Am. J. Physiol. 257: F1059 (1989).
McCarthy, D.W., et al. "Production of heparin–binding epidermal growth factor–like growth factor (HB–EGF) at sites of thermal injury in pediatric patients." J. Invest. Dermatol. 106: 49 (1996).
Marikovsky, M., et al. "Appearance of heparin–binding EGF–like growth factor in wound fluid as a response to injury." Proc. Natl. Acad. Sci USA 90: 3889 (1993).
Homma, T., et al. "Induction of heparin–binding epidermal growth factor–like growth factor mRNA in rat kidney after acute injury." J. Clin. Invest. 96: 1018 (1995).
deBoer, W.I., et al. "Characterization of distinct functions for growth factors in murine transitional epithelial cells in primary organotypic culture." Exp. Cell Res. 214: 510 (1994).

(List continued on next page.)

*Primary Examiner*—Elizabeth Kemmerer
*Assistant Examiner*—Regina M. DeBerry
(74) *Attorney, Agent, or Firm*—Steven J. Hulquist; Marianne Fuierer

(57) ABSTRACT

Interstitial cystitis (IC) is a chronic bladder disease for which the exact etiology is unknown and for which there is no reliably effective treatment. However, it is known that the bladder epithelium is often abnormal in IC. We discovered that normal, adult, human bladder epithelial cells are inhibited from proliferating by an anti-proliferative factor (APF) present in IC urine specimens. Inhibited proliferation may cause epithelial abnormalities characteristic of IC such as ulcerations and multiple tears in the bladder epithelium. We further discovered that levels of heparin binding—epidermal growth factor-like growth factor (HB-EGF), a factor known be important for epithelial cell proliferation and wound healing in other tissues, are abnormally low in the urine of patients suffering from IC as compared to asymptomatic controls or patients with acute bacterial cystitis. The invention herein is directed to the use of urine levels of HB-EGF as a diagnostic marker for IC.

13 Claims, 5 Drawing Sheets

OTHER PUBLICATIONS

Jorgensen, P.E., et al. "Urinary epidermal growth factor is excreted from the rat isolated perfused kidney in the absence of plasma." J. Endocrinol. 139: 227 (1993).

Southgate, J., et al. "Normal human urothelial cells in vitro: proliferation and induction of stratification." Lab. Invest. 71: 583 (1994).

Chin, E. et al. "Insulin–like growth factor system gene expression in the human kidney." J. Cin. Endocrinol. Metab. 75: 962 (1992).

Jones, J.I., et al. "Insulin–like growth factors and their binding proteins: biological actions." Endocrine Rev. 16:3 (1995).

Freeman, M.R., et al. "Human urothelial cells secrete and are regulated by heparin–binding epidermal growth factor–like growth factor (HB–EGF)." Proc. Am. Urol. Assoc. 153: 316A (1995).

Tobin, M.S., et al. "Growth factor biology of human urothelial cells grown under serum–free conditions." Proc. Am. Urol Assoc. 153; 406A (1995).

Division of Kidney, Urolog, and Hematologic Diseases (DKUHD) of the National Institute of Diabetes and Digestive and Kidney Diseases (NIDDK). "Diagnostic criteria for research studies (interstitial cystitis)." Am. J. Kidney Dis. 13:353 (1989).

Third Symposium on Insulin–like Growth Factors. "Valid measurements of total IGF concentrations in biological fluids." Endocrinology 136: 816 (1995).

Schirmeister, J., et al. "Plasmakreatinin alf grobher indikator der nierenfunktion." Dtsch. Med. Wschr. 89: 1018 (1964).

Shishido, Y., et al. "Heparin–like molecules on the cell surface potentiate binding of diphtheria toxin to the diphtheria toxin receptor/membrane–anchored heparin–binding epidermal growth factor–like growth factor," J. Biol. Chem. 271: 29578 (1995).

Erickson, D.R. and Davies, M.F. "Interstitial Cystitis." Int. Urogynecol. J. Pelvic Floor Dysfunct. 9(3): 174–183 (1998).

Cribbs, R.K. et al. "Acceleration of Partial–thickness Burn Wound Healing with Topical Application of Heparin–binding EGF–Like Growth Factor (HV–EGF)" J. Burn Care Rehabil. 19(2): 95–101 (1998).

Sant, G.R. and Theohardies, T.C. "Interstitial Cystitis." Curr. Opi. Urol. 9(4): 297–302 (1999).

Keay et al. "Decreased $^3$H–Thymidine Incorporation by Human Bladder Epithelial Cells Following Exposure to Urine From Interstitial Cystitis Patients" J. Urol. 156(6):2073–2078 (1996).

Göran L. Matejka et al. "IGF–I Binding and IGF–I mRNA Expression in the Post–Ischemic Regenerating rat Kidney" Kidney Int'l 42:1113–1123 (1992).

Moxham, et al. "Insulin action impaired by deficiency of the G–protein subunit $G_{i\alpha 2}$" Letters to Nature 379:840–844 (1996).

Keay et al. "A prospective study of microorganisms in urine and bladder biopsies from interstitial cystitis patients and controls" Adult Urology 45(2):223–229 (1995).

Quattrin, et al. "Comparison of urinary growth hormone and IGF–I expression in small– and appropriate–for–gestational age infants and healthy children" Pediatric Research 28(3):209–212 (1990).

Dreyer, et al. "Prolonged plasma half–life of insulin in patients with a genetic defect of high affinity binding sites" Horm metabol. Res. 18:247–249 (1986).

Burgess, W.H. et al. "Possible Dissociation of the Heparin–binding and Mitogenic Activities of Heparin–binding (Acidic Fibroblast) Growth Factor–1 from Its Receptor–binding Activities by Site–Directed Mutagenesis of a Single Lysine Residue", *J. Cell Biology.* vol. 111. Nov. 1990. 2129–2138.

Lazar, E., et al. Transforming Growth Factor.

* cited by examiner

DIAGNOSIS OF INTERSTITIAL CYSTITIS

CROSS-REFERENCE TO RELATED APPLICATIONS

The present application is a divisional of U.S. patent application Ser. No. 09/109,548 now U.S. Pat. No. 6,156,522 filed Jul. 2, 1998.

This application claims priority to provisional U.S. patent application Ser. No. 60/051,458, filed Jun. 30, 1997, entitled "Concentrations of Heparin Binding—Epidermal Growth Factor in the Urine of Interstitial Cystitis Patients and Controls". This application is related to pending non-provisional U.S. patent application Ser. No. 08/944,202 now U.S. Pat. No. 5,962,645, filed Oct. 3, 1997, entitled "A Novel Anti-proliferative Factor from Patients with Interstitial Cystitis" and pending provisional U.S. patent application Ser. No. 60/082,070, filed Apr. 17, 1998, entitled "Method Of Treating Interstitial Cystitis With Recombinant Heparin-Binding Epidermal Growth Factor-Like Growth Factor (HB-EGF)."

SPONSORSHIP

Support for the research disclosed herein was provided by the University of Maryland, Baltimore and the Interstitial Cystitis Association.

FIELD OF THE INVENTION

The field of this invention specifically relates to the diagnosis of Interstitial Cystitis (IC) by measuring levels of HB-EGF in the urine of IC patients.

BACKGROUND OF THE INVENTION

Interstitial cystitis (IC) is a chronic inflammatory disease of the bladder for which the etiology is unknown. IC often has a rapid onset with pain, urgency and frequency of urination, and cystoscopic abnormalities including petechial hemorrhages (glomerulations) or ulcers that extend into the lamina propria (Hunner's ulcers)[1,2]. The rapid onset of IC is followed by a chronic course with partial remissions and re-exacerbations, which can continue for up to 30 years[1,2]. As a result of the absence of a specific cause for and lack of understanding of its pathogenesis, there is currently no generally accepted treatment proven to be reliably efficacious.

Various groups have studied IC and speculated as to its cause. Proposed etiologies include infection, allergic or immune disorders, endocrinologic disturbance, toxic urinary chemicals, defective transitional mucosa, psychiatric disorders, neurogenic disorders, lymphatic obstruction, or vascular obstruction. Proposed treatments include pentosan polysulfate, anti-inflammatory or immunosuppressant therapy, muscle relaxants, anti-histamines, and analgesics. Of these, only pentosan polysulfate has been approved by the FDA. However, none of the proposed therapies, including pentosan polysulfate, is universally accepted or universally efficacious. As a result, there is a long felt need for adequate therapy of this poorly understood and frequently misdiagnosed disorder.

Certain morphologic and histologic features of IC suggest that the epithelium is usually abnormal in this disease[3-5], with evidence for changes in the bladder mucin layer[6], denudation or thinning of the bladder epithelium and rupture of the mucosa[3-5,7], and intraurothelial infiltration of urinary proteins such as Tamm-Horsfall protein[8]. In addition, activation of bladder epithelial cells appears to be abnormal in IC, with altered expression of specific cellular proteins[9]. These changes coupled with the chronic nature of IC suggests the possibility of impaired regeneration of normal bladder epithelium. In previous experiments, we discovered a 1–3 kDa peptide in the urine of IC patients that inhibits the proliferation of cultured normal adult human bladder epithelial cells, suggesting that it may be related to the pathogenesis of this disorder (see co-pending application Ser. No. 08/944,202 now U.S. Pat. No. 5,962,645). This peptide is hereafter referred to as the anti-proliferative factor or APF.

The uninjured postnatal urothelium regenerates very slowly, but rapid proliferation of uroepithelial cells in vivo can occur during tissue regeneration in response to injury[10]. The limited data that exist for bladder epithelial cells suggest their replication and differentiation are probably influenced by specific paracrine or autocrine growth factors and their regulatory proteins, similar to other types of epithelial cells[10-21]. Epithelial cell growth factors known to be present in normal human urine include epidermal growth factor (EGF), insulin-like growth factors (IGF's), insulin-like growth factor binding proteins (IGFBP's), heparin-binding epidermal growth factor-like growth factor (HB-EGF), platelet-derived growth factors (PDGF-A and B), fibroblast growth factors (FGF1 and 2), and transforming growth factor beta (TGFβ). EGF, which is produced primarily by cells in the thick ascending limb of Henle and the distal convoluted tubule[22], is present in high concentrations in urine, and can stimulate, but is not required for, mouse bladder epithelial cell proliferation in vitro[23]. IGF1 and IGF2 are produced by both kidney and bladder cells and appear to be required for bladder epithelial cell proliferation[10,21,24]. The major IGFBP's found in human urine, which can regulate the activity of IGF1 and 2 are IGFBP-2 and IGFBP-3[25]. HB-EGF is also known to be produced by human bladder epithelial cells and can stimulate their growth in vitro[26,27]. In contrast, current data suggest that the PDGF's, FGF's and TGFβ affect bladder epithelial cell migration and/or differentiation, but their role in cell proliferation remains uncertain[10,21].

Exogenously applied growth factors can stimulate epithelial wound repair[11-13]. Since IC is histologically characterized by epithelial abnormalities and because the mucosal defects present in IC result in exposure of basal undifferentiated cells and their growth factor receptors to urine growth factors, we reasoned that abnormally low levels of urinary growth factors, such as HB-EGF, that stimulate bladder epithelial cell proliferation could adversely affect bladder epithelial wound repair and be part of the etiology of IC.

We measured urinary levels of HB-EGF in women with IC, asymptomatic control women without bladder disease, and women with acute, self-limited bladder epithelial damage from bacterial cystitis. We discovered that urine levels of HB-EGF are specifically and significantly decreased in the urine of IC patients.

Based on the above, we have concluded that urine levels of HB-EGF may be used for diagnosing Interstitial Cystitis (IC).

SUMMARY OF THE INVENTION

Human bladder epithelial cells are known to produce HB-EGF[26]. Since IC is histologically characterized by epithelial abnormalities and because the mucosal defects present in IC result in exposure of basal undifferentiated cells and their growth factor receptors to urine growth factors, we reasoned that abnormally low levels of urinary growth factors, such as HB-EGF, that stimulate bladder epithelial cell proliferation could adversely affect bladder epithelial wound repair and be part of the etiology of IC.

It is the object of the invention to provide a reliably effective diagnostic for diseases associated with inhibited epithelial cell proliferation, particularly bladder epithelial cell proliferation, more particularly interstitial cystitis (IC), using heparin-binding epidermal growth factor-like growth factor (HB-EGF) which is capable of inhibiting the anti-proliferative activity present in most IC urine specimens. Our findings indicate that complex changes in the levels of urine growth factors are associated with IC, including significant and specific decreases in BB-EGF levels in the urine of IC patients.

DETAILED DESCRIPTION OF THE INVENTION

Figure 1A:
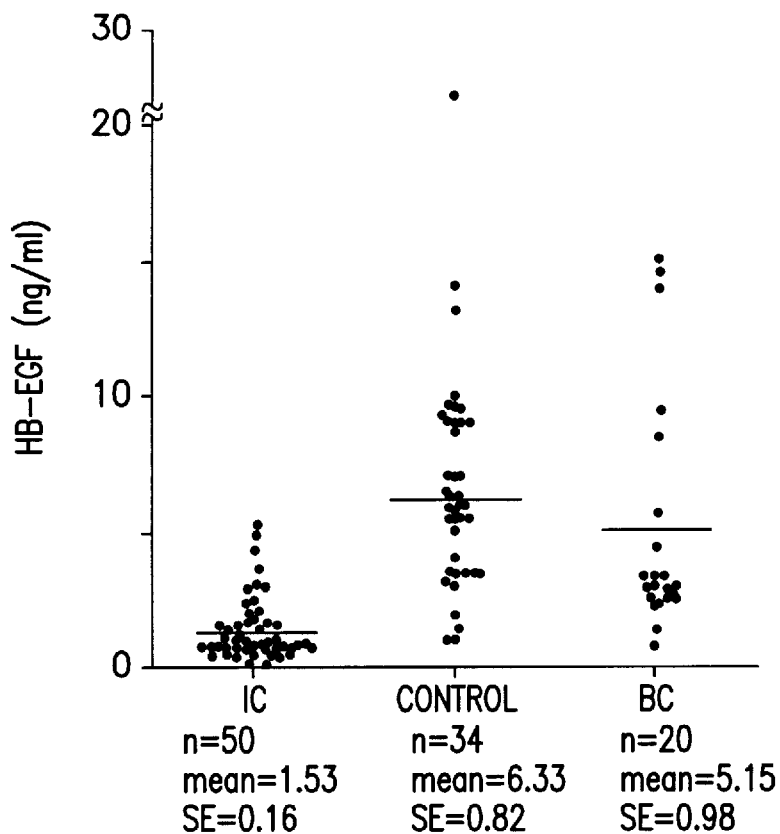
FIGS. 1A–1B: Depicts concentrations of HB-EGF in urine specimens from women with IC, asymptomatic control women without bladder disease, and women with acute, self-limited bladder epithelial damage from bacterial cystitis.

Interstitial cystitis (IC) is a chronic bladder disease for which the etiology is unknown and for which there is no effective and reliable therapy. The bladder epithelium is often abnormal in IC. Therefore, we reasoned that the levels of epithelial growth factors such as heparin-binding epidermal growth factor-like growth factor (HB-EGF) might be important for bladder epithelial proliferation. ELISAs were used to determine levels of heparin binding epidermal growth factor-like growth factor (HB-EGF) as well as other growth factors in urine specimens from women with IC, asymptomatic control women without bladder disease, and women with acute, self-limited bladder epithelial damage from bacterial cystitis. The levels of the other growth factors assayed in urine from IC patients proved to be slightly elevated when compared to urine from normal and bacterial cystitis controls (See FIGS. 2–4). However, urine HB-EGF levels were specifically and significantly decreased in IC patients as compared to asymptomatic controls or patients with bacterial cystitis, whether expressed as concentration (amount per volume of urine) or the amount relative to creatinine in each specimen (See FIG. 1). These findings indicate that complex changes in the levels of urine growth factors are associated with IC, including significant and specific decreases in HB-EGF levels in the urine of IC patients.

With the above information in hand, we proceeded to determine whether the measurement of HB-EGF levels in urine could be used as a diagnostic for IC. An optimal sensitivity and specificity of 0.84 and 0.82, respectively, can be achieved at a cut-off value of 2.9 ng of HB-EGF per ml of urine, making urine HB-EGF measurements useful for a diagnostic assay for IC.

Experimental Data

A. Materials and Methods

Patients

IC patients were referred by physicians, the National Institute of Diabetes and Digestive and Kidney Diseases (NIDDK), and the Interstitial Cystitis Association. All IC patients had previously undergone diagnostic cystoscopy, and fulfilled the NIDDK diagnostic criteria for IC[28]. For preliminary studies performed at the University of Maryland School of Medicine, urine was collected from the IC patients at least three months following the most recent know bacterial urinary tract infection and one month following the last antibiotic use. Age-, race-, and sex-matched controls were-volunteers with no history of IC or other urological disease. Each control patient was required to have no symptom of urinary tract infection or antibiotic use for the last month. Urine specimens collected at the University of Pennsylvania for additional studies were obtained during routine office visits for management of IC. Patients with acute bacterial cystitis were identified at the University of Maryland School of Medicine and the University of Maryland—College Park by the presence of bacterium ($>10^3$ bacteria/ml with single type of bacterium isolated) plus pyuria in combination with appropriate symptoms. Twelve (12) of the fifteen (15) patients has $>10^5$ bacteria/ml. All participants were at least 18 years old and enrolled in accordance with guidelines of the Institutional Review Boards at the University of Maryland School of Medicine, the University of Maryland, College Park, and the University of Pennsylvania.

Urine Specimens

Urine was collected by the clean catch method in which each patient wiped the labial area with 10% povidone iodine/titratable iodine 1% solution [Clinidine, Guilford, Conn.], then collected a midstream urine into a sterile container. Specimens obtained at the University of Maryland for preliminary studies (IC patients; age-, race-, and sex-matched controls; and bacterial cystitis patients) were initially kept at 4 degrees C., then transported to the laboratory where cellular debris was removed by the low speed centrifugation at 4 degrees C. Specimens obtained at the University of Pennsylvania (from IC patients only) and the University of Maryland, College Park (from bacterial cystitis patients only) for confirmatory studies were frozen at −20 degrees C. for up to 4 weeks, then transported to the University of Maryland School of Medicine on ice. All specimens were subsequently aliquoted under sterile conditions, and stored at −80 degrees C. until used.

ELISAs

Figure 1B:
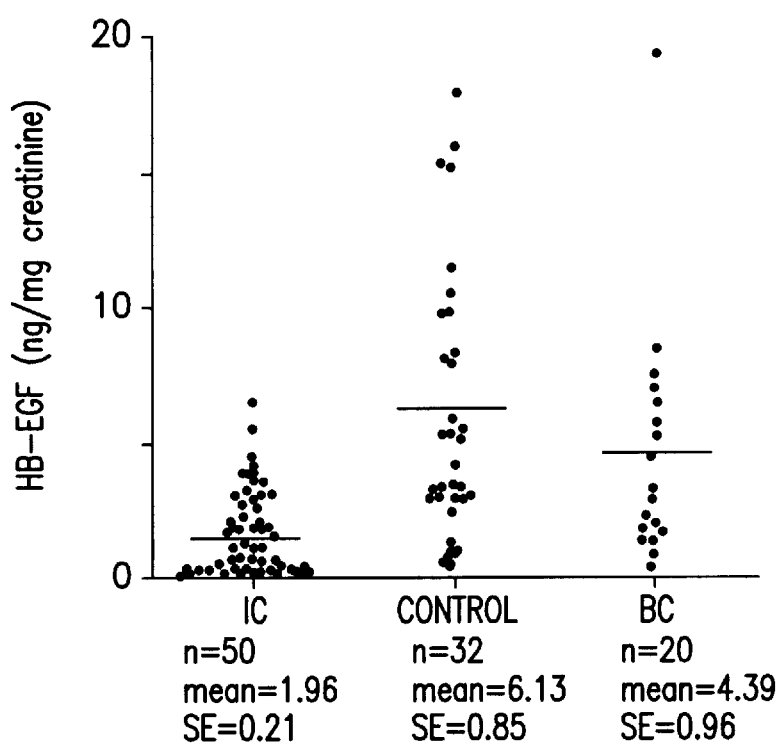

1) HB-EGF (FIGS. 1A and 1B)

To assay for the levels of HB-EGF in urine, each well of a 96 well Immulon II plate (Dynatech Laboratories, Chantilly, Va.) was coated with 200 λ urine at 4 degrees C. overnight. Following 5 washes with phohsphate buffer the plates were blocked with 5% fetal bovine serum/1 mM EDTA/0.05% Tween 20 in PBS. Anti-HB-EGF antibody (1 µg/ml) (R & D Systems, Minneapolis, Minn.) was added and the plates were incubated for 2 hours at 37 degrees C. Following an additional 5 washes, biotinylated anti-goat IgG/avidin D horseradish peroxidase was added and plates were incubated for 1.5 hours at room temperature, washed, and developed with ABTS [2,2'-Azino-bis-(3-ethylbenzothiazoline-6-sulfonic)] substrate. Absorbance was read at 405 nm.

Figure 2A:
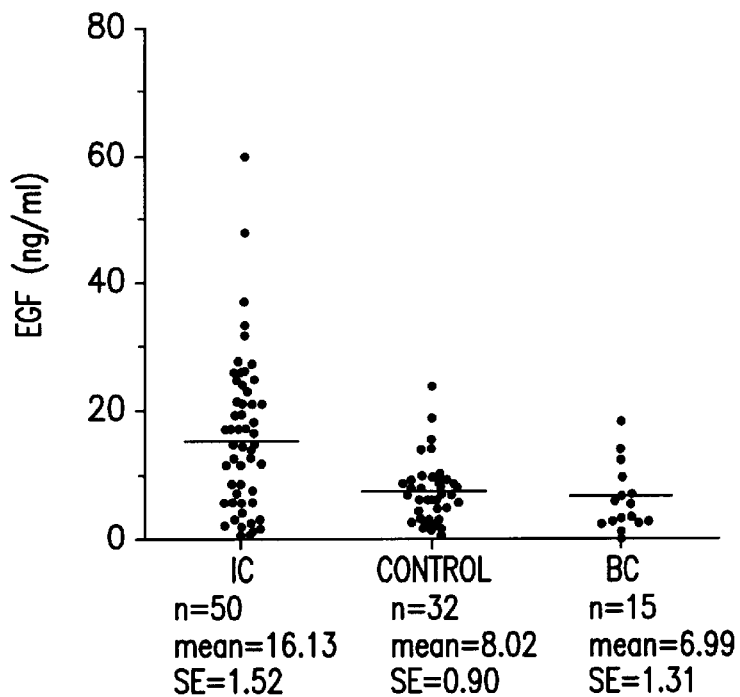
FIGS. 2A–2B: Depicts concentrations of EGF in urine specimens from women with IC, asymptomatic control women without bladder disease, and women with acute, self-limited bladder epithelial damage from bacterial cystitis.
Figure 2B:
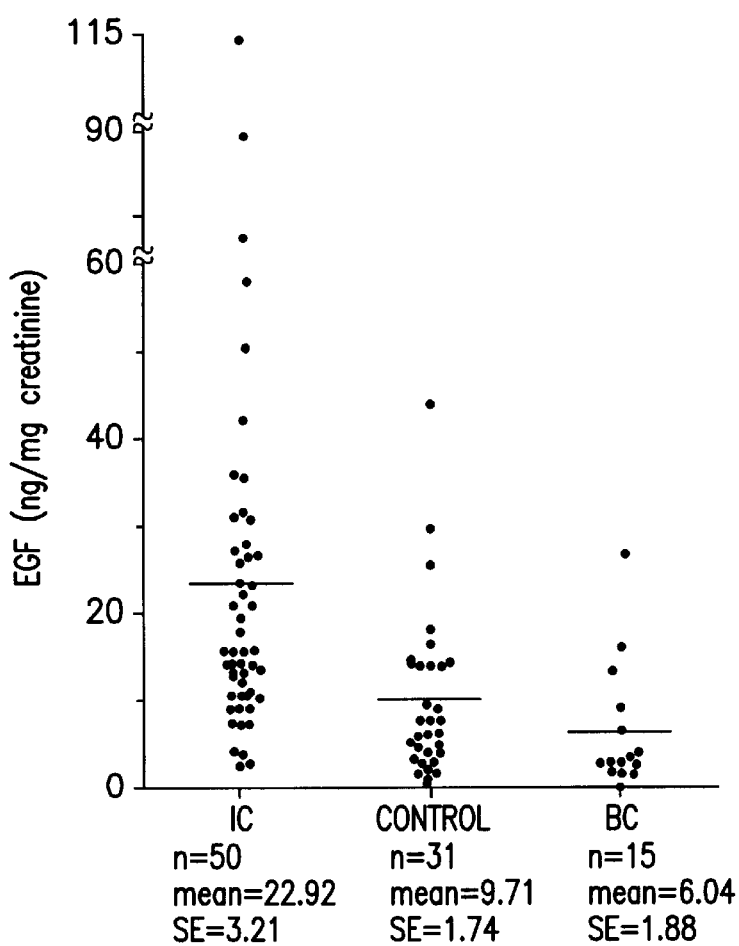

2) EGF (FIGS. 2A and 2B)

For determination of EGF levels, urine from IC patients and controls was diluted 1:200–1:300 in RD5E diluent and pipetted into wells precoated with monoclonal anti-EGF antibody, according to the manufacturer's instructions (R & D Systems, Minneapolis, Minn.). Following incubation at room temperature for 4 hours, plates were washed with phosphate buffered saline (PBS) and incubated further with HRP-linked polyclonal anti-EGF, washed, and developed with tetramethylbenzidine (TMB) substrate; development was stopped with 0.2 M $H_2SO_4$.

Figure 3A:
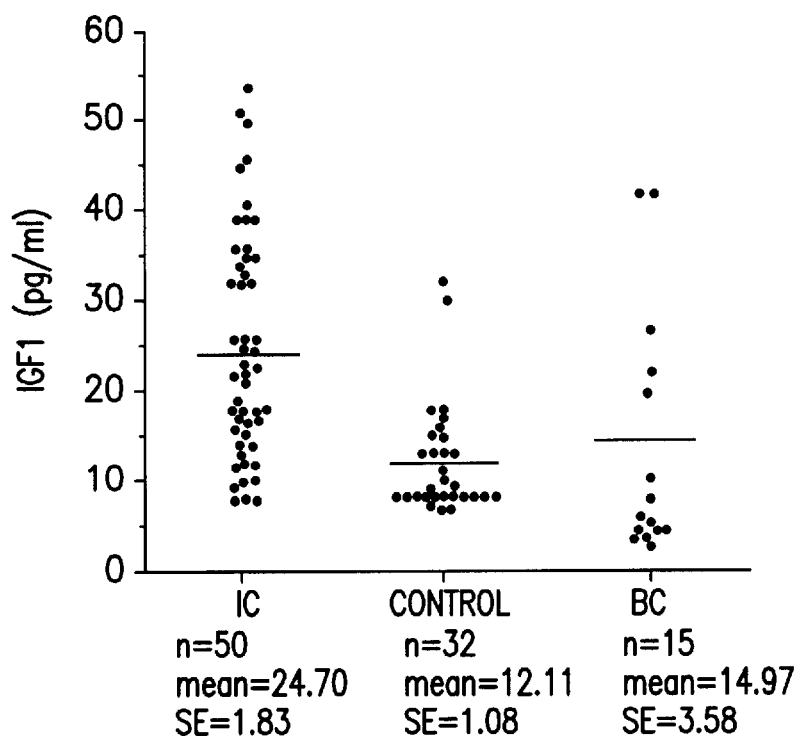
FIGS. 3A–3B: Depicts concentrations of IGF-1 in urine specimens from women with IC, asymptomatic control women without bladder disease, and women with acute self-limited bladder epithelial damage from bacterial cystitis.
Figure 3B:
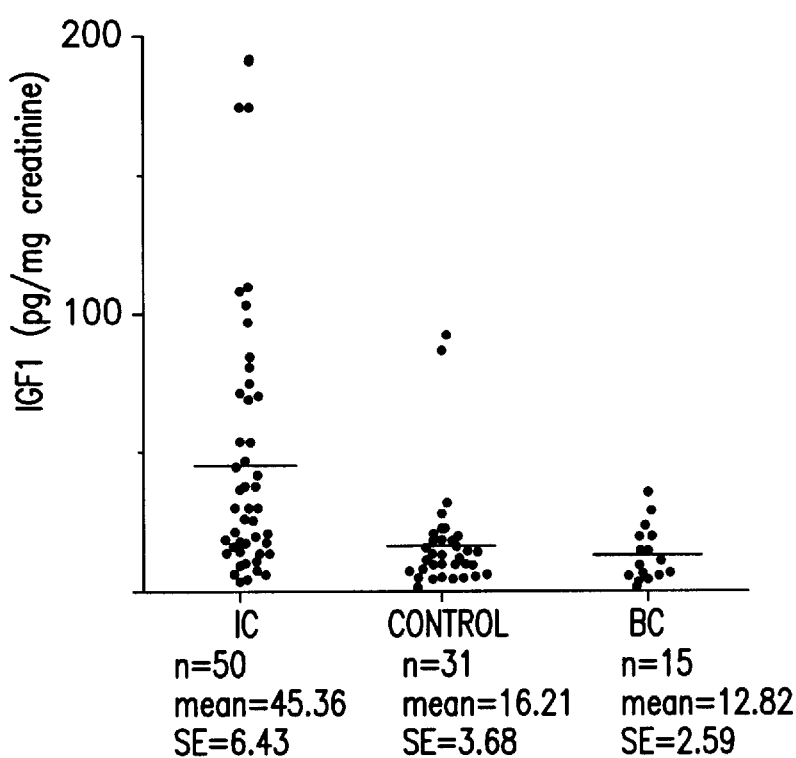

3) IGF1 (FIGS. 3A and 3B)

Total IGF1 levels were also measured by ELISA (Diagnostic Systems Laboratories, Webster, Tx.). Urine for these determinations was concentrated 30-fold by lyophilization and reconstitution in ethanolic HCl in accordance with published recommendations[29]. After 30 minutes incubation at room temperature, samples were centrifuged at 10,000 rpm for 3 minutes to remove insoluble material, and supernatant neutralized to pH 7 with neutralization buffer. Neutralized, extracted samples were added to wells along with anti-IGF HRP-conjugate, and plates were incubated for 2 hours at room temperature. Following washes, plates were developed with TMB chromogen solution; development was stopped with 0.2 M $H_2SO_4$.

Figure 4A:
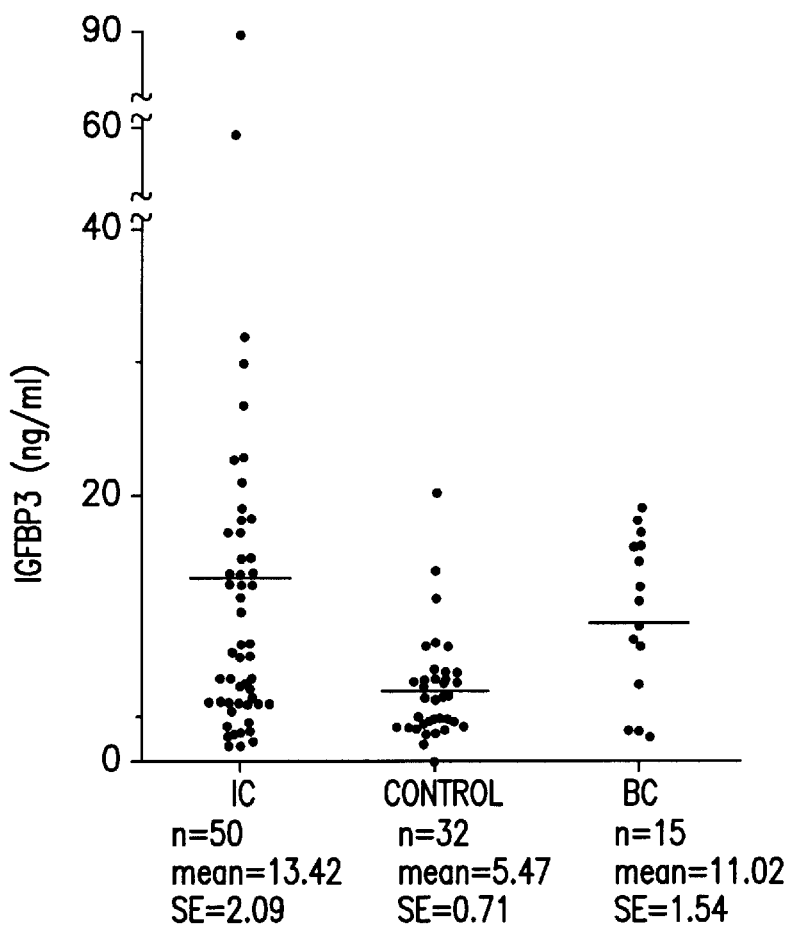
FIGS. 4A–4B: Depicts concentrations of IGFBP-3 in urine specimens from women with IC, asymptomatic control women without bladder disease, and women with acute, self-limited bladder epithelial damage from bacterial cystitis.
Figure 4B:
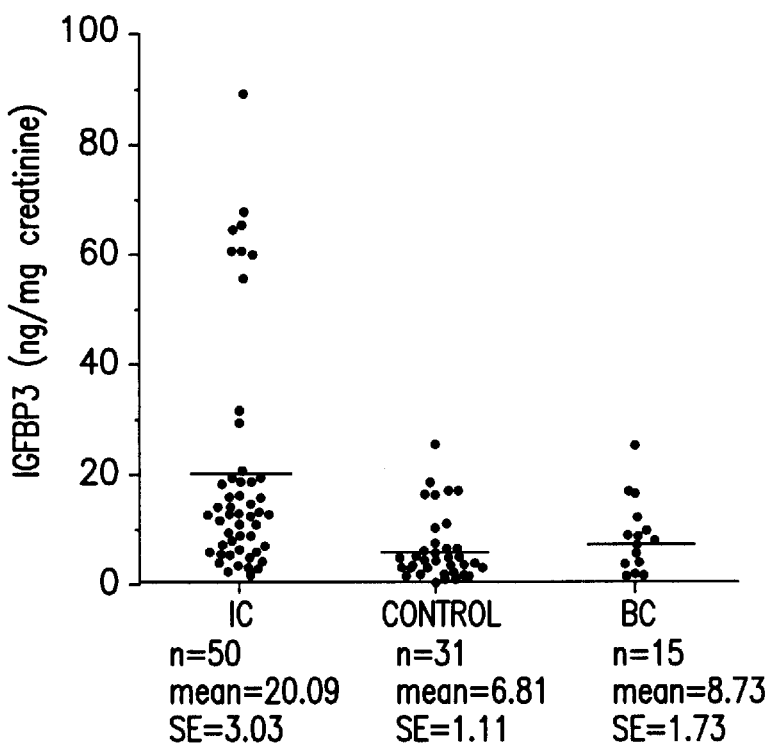

4) IGFBP3 (FIGS. 4A and 4B)

For determination of IGFBP3 levels, undiluted urine specimens were added to wells precoated with polyclonal anti-IGFBP3, then incubated at room temperature for 2 hours. Following washes, another polyclonal, HRP-labeled anti-IGFBP3 antibody was added to the wells, and the plates were further incubated, washed, and developed with TMB substrate; development was stopped with 0.2 M $H_2SO_4$.

For each protein measured, linear absorbance vs. concentration curves were prepared from results with known standard concentrations of recombinant growth factor or growth factor binding protein, and urine sample EGF, IGF1, IGFBP3 and HB-EGF concentrations were plotted. (See FIGS. 1–4).

Measurement of Urinary Creatinine

Urinary creatinine was measured by the Jaffe method, using picric acid, as previously described[30]. Data were then expressed as both the amount of each growth factor or binding protein present per volume of urine or per milligram of urine creatinine. The latter allows the values to be normalized to kidney function (excretion rate), thereby eliminating variables due to volume produced (excretion volume).

Statistical Analysis:

For the preliminary studies, comparisons of mean difference in HB-EGF levels in urine specimens from IC patients vs. age-, race- and sex-matched controls were performed using a two-way analysis of variance, with age and case-control status as the two factors. For the confirmatory studies with larger sample populations of women with IC, asymptomatic control women, and women with bacterial cystitis, comparisons of mean difference in growth factor levels were performed using a two-tailed analysis of covariance with age as the covariate.

Logistic regression analysis was performed with case or control status serving as the dependent variable and the amount of HB-EGP serving as the independent variable. Both HB-EGF concentration per milliliter of urine and HB-EGF concentration per mg of urine creatinine were analyzed. Sensitivity and specificity were derived from the logistic regression model, and the sensitivity and specificity determined for various cutoff values.

B. Results

We determined the levels of HB-EGF in urine specimens from women with IC, asymptomatic control women, and women with bacterial cystitis. The quantity of inmmunoreactive HB-EGF in the urine of IC patients was markedly decreased as compared to asymptomatic controls, reaching significance at the level of p<0.001 in both the preliminary analysis (in which age-, race- and sex-matched asymptomatic controls were used) and the subsequent larger analysis (in which women with IC, asymptomatic women, and women with bacterial cystitis were studied). As shown in FIG. 1A, the concentration of HB-EGF was strikingly lower in IC patient specimens (1.53±0.16 ng/ml) as compared to asymptomatic controls (6.33±0.82 ng/ml, p<0.001) or patients with bacterial cystitis (5.15±0.98 ng/ml p<0.001), with 37 of 50 IC patients (74%) having levels below 2 ng/ml. The levels of HB-EGF were also significantly lower in IC specimens than in urine from either control group when data were expressed per milligram of urine creatinine (p<0.001 and p=0.028, respectively) (FIG. 1B).

Figure 5:
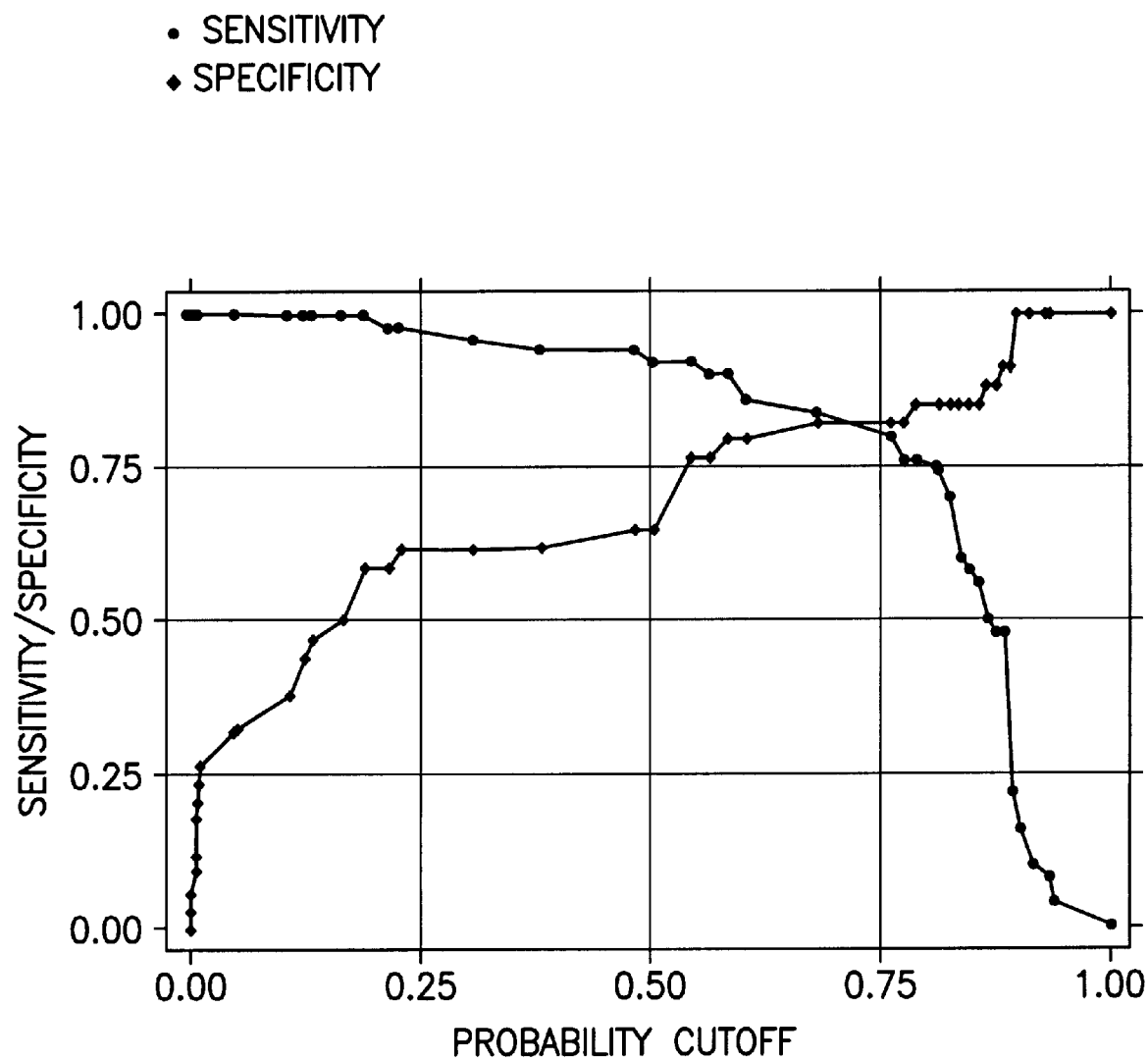
FIG. 5: Using the data depicted in FIG. 1A, sensitivity and specificity curves were generated for the measurement of urine HB-EGF levels as a diagnostic parameter for IC. The crossover point indicates the optimal sensitivity and specificity levels of 0.84 and 0.82, respectively. This optimum point, achieved using a cut-off value of 2.9 ng HB-EGF per ml of urine, indicates that HB-EGF has utility as a diagnostic marker for IC.

Sensitivity and specificity measurements (FIG. 5) were derived from the logistic regression analysis, and a sensitivity of 84% and a specificity of 82% were achievable at a cutoff value of 2.9 ng HB-EGF per ml urine. (A similar analysis of ng HB-EGF per mg urine creatinine indicated lower achievable sensitivity of 72% with a specificity of 75%). If a cutoff value of 5.0 ng HB-EGF per ml urine was used, 98% sensitivity was achievable with a specificity of 59%. These findings indicate that measuring the concentration of urine HB-EGF per ml urine is useful for the diagnosis of IC, either as a single assay with a cutoff of 2.9 ng/ml or as a screening assay with a cutoff of 5.0 ng/ml. The positive predictive value of the assay at the 2.9 ng/ml cut-off point is 72%; the negative predictive value is 91%.

Although differences in urine levels of other growth factors (such as EGF, IGF1) or binding proteins (such as IGFBP3) could also be demonstrated between IC patients and controls, none of these was as sensitive or specific for the diagnosis of IC as differences in urine levels of HB-EGF. With respect to the data shown in FIG. 2, studies indicated a trend toward higher mean concentrations of immunoreactive EGF in IC specimens (16.13±1.52 ng/ml) as compared to asymptomatic controls (8.02±0.90 ng/ml) or patients with bacterial cystitis (6.99±1.31 ng/ml) (p<0.001 for both comparisons) (See FIG. 2A). Similar results were obtained when the amount of EGF was expressed per milligram of urine creatinine (p=0.001 for a comparison of IC and bacterial cystitis patients) (see FIG. 2B).

With respect to FIG. 3, quantities of immunoreactive IGF1 in the urine were measured because of the recognized importance of both IGF1 and IGF2 for bladder epithelial cell proliferation in vitro. A significant increase in urine IGF1 levels was evident in IC patients (24.70±1.83 pg/ml) as compared to asymptomatic controls (12.11±1.08 pg/ml, p<0.001) or specimens from bacterial cystitis patients (14.97±3.58 pg/ml, p=0.01) (see FIG. 3A). This finding was similarly true if the amount of urine IGF1 was expressed per milligram of urine creatinine (p<0.001 and p=0.001, respectively) (see FIG. 3B).

With respect to FIG. 4, the activity of the IGF's is modified by IGFBP's. IGFBP's or their peptides (generated by specific proteases) can have their own direct stimulatory or inhibitory effects on epithelial cells via IGFBP receptors. We chose to measure IGFBP3 as one of the predominant IGFBP's in urine. Our studies indicated that the concentration of IGFBP3 was significantly higher in the urine of IC patients (13.42±2.09 ng/ml) as compared to asymptomatic controls (5.47±0.71 ng/ml, p=0.001) (see FIG. 4A). This finding was so true when data were expressed per milligram of urine ceatinine (20.09±3.03 ng/ml vs. 6.81±1.11 ng/ml, p<0.001) (see FIG. 4B). However, the difference in concentration of urine IGFBP3 between IC and bacterial cystitis patients did not achieve statistical significance (13.42±2.09 ng/ml vs. 11.02±1.54 ng/ml, p=0.55) (see FIG. 4A). When expressed per mg of urine creatinine, the difference was statistically significant (20.09±3.03 ng/ml for IC patients vs. 8.73±1.73 ng/ml for bacterial cystitis patients, p=0.004) (see FIG. 4B). The ratio of IGF1 to IGFBP3 was also calculated for IC patients and their controls. Although there was a trend toward a lower ratio in the IC patients' urine than in urine from asymptomatic controls, the difference in IGF1:IGFBP3 between the two groups did not reach statistical significance (p=0.09).

C. Discussion

The limited data that exist for bladder epithelial cell growth suggest that replication and differentiation are influenced by growth factors and regulatory proteins of growth factors. Of greatest interest as potential stimulators of bladder epithelial cell replication is HB-EGF, which is produced by bladder epithelial cells and can stimulate their growth in vitro[26,27]. HB-EGF is produced by both kidney and bladder epithelial cells[20,24,26]. HB-EGF is capable of autocrine and/or paracrine activity, having effects on the cell of origin as well as neighboring or distant cells within the urinary tract. HB-EGF was specifically decreased in the urine of IC patients as compared to both asymptomatic controls and patients with bacterial cystitis. This decrease could also occur as a result of other inherent abnormalities in IC that secondarily affect HB-EGF synthesis which may or may not be causally related to the disease process. Because HB-EGF is produced by bladder epithelial cells, it is conceivable that urine levels of this growth factor may be secondarily decreased as a result of thinning and denudation of epithelial cells as seen in IC. Furthermore, epithelial cell surface glycosaminoglycans, which are commonly decreased in IC[6], can influence binding to the HB-EGF receptor[31] and could therefore influence HB-EGF production secondarily. However, HB-EGF has been shown to be important for replication of a variety of epithelial cells including hepatocyte, keratinocytes, gastric epithelial cells, and uterine epithelial cells, and is known to stimulate bladder epithelial replication in vitro[18-20,26,27]; it is therefore possible that decreased synthesis of HB-EGF by epithelial or other bladder cells contributes to the pathogenesis of IC by impairing normal bladder epithelial regeneration.

IC is currently diagnosed by cystoscopy. Although various markers have been suggested for IC, none has yet been shown to be clinically useful. The differences in mean urine concentrations of HB-EGF between IC patients and controls were greater than one standard deviation, suggesting that the concentration of HB-EGP is useful as a diagnostic marker for IC. Determination of assay sensitivity and specificity at different cut-off values confirmed the usefulness of this assay.

REFERENCES

1. Hanno, P. M., Staskin, D. R., Krane, R. J., and Wein, A. J., eds. *Interstitial Cystitis*. London: Springer-Verlag, 1990.
2. Held, P. J., Hanno, P. M., Wein, A. J., Pauly, M. V., and Cann, M. A.: *Epidemiology of interstitial cystitis:* 2. In: *Interstitial Cystitis*. Edited by P. M. Hanno, D. R. Staskin, R. J. Krane, and A. J. Wein. London: Springer-Verlag, pp. 29–48, 1990.
3. Johansson, S. L. and Fall, M. Clinical features and spectrum of light microscopic changes in interstitial cystitis. J. Urol., 143: 1118, 1990.
4. Oravisto, K. J., Alfthan, O. S. and Jokinen, E. J. Interstitial cystitis: Clinical and immunological findings. Scand. J. Urol. Nephrol., 4: 37, 1970.
5. Skoluda, D., Wegner, K. and E.-M. Lemmel. Kritische Bemerkungen zur Immunopathogenese der interstitiellen Cystitis. Urologe, 13: 15, 1974.
6. Parsons, C. L., Lilly, J. D. and Stein, P. Epithelial dysfunction in nonbacterial cystitis (interstitial cystitis). J. Urol., 145: 732, 1991.
7. Smith, B. H. and Dehner, L. P. Chronic ulcerating interstitial cystitis (Hunner's ulcer), Arch. Path., 93: 76, 1972.
8. Fowler, J., Jr, Lynes, W. L., Lau; J. L. T., Ghosh, L., and Mounzer, A. Interstitial cystitis is associated with intraurothelial Tamm-Horsfall protein. J. Urol., 140:1385, 1988.
9. Liebert, M., Wedemeyer, G. Stein, J. A., Washington, R., Jr., Faerber, G., Fint, A. and Grossman, H. B. Evidence for urothelial cell activation in interstitial cystitis. J. Urol., 149: 470, 1993.
10. deBoer, W. I., Schuller, A. G. P., Vermey, M., and van der Kwast, T. H. Expression of growth factors and receptors during specific phases in regenerating urothelium after acute injury in vivo. Am. J. Pathol. 145: 1199, 1994.
11. Lynch, S. E., Colvin, R. B., and Antoniades, H. N. Growth factors in wound healing. Single and synergistic effects on partial thickness porcine wounds. J. Clin. Invest. 84: 640, 1989.
12. Mustoe, T. A., Pierce, G. F., Morishima, C., and Deuel, T. F. Growth factor-induced acceleration of tissue repair through direct and inductive activities in a rabbit dermal ulcer model. J. Clin. Invest. 87: 694, 1991.
13. Mellin, T. N., Mennie, R. J., Cashen, D. E., Ronan, J. J., Capparella, J., James, M. L., Disalvo, J., Frank, J., Linemeyer, D., Giminez-Gallego, G., and Thomas, K. A. Acidic fibroblast growth factor accelerates dermal wound healing. Growth Factors 7: 1, 1992.
14. Antoniades, H. N., Galanopoulos, T., Neville-Golden, J., Kiritsky, C. P., and Lynch, S. E. Expression of growth factor and receptor mRNAs in skin epithelial cells following acute cutaneous injury. Am. J. Pathol. 142: 1099, 1993.
15. Werner, S., Peters, K. G., Longaker, M. T., Fuller-Pace, F., Banda, M. J., and Williams, L. T. Large induction of keratinocyte growth factor expression in the dermis during wound healing. Proc. Natl. Acad. Sci. USA 89: 6896, 1992.
16. Nusrat, A., Parkos, C. A., Bacarra. A. E., Godowski, P. J., Delp-Archer, C., Rosen, E. M., and Madara, J. L. Hepatocyte growth factor/scatter factor effects on epithelia. J. Clin. Invest. 93: 2056, 1994.

17. Behrens, M. T., Corbin, A. L., and Hise, M. K. Epidermal growth factor receptor regulation in rat kidney: two models of renal growth. Am. J. Physiol. 257: F1059, 1989.
18. McCarthy, D. W., Downing, M. T., Brigstock, D. R., Luquette, M. H., Brown, K. D., Abad, M. S., and Besner, G. E. Production of heparin-binding epidermal growth factor-like growth factor (HB-EGF) at sites of thermal injury in pediatric patients. J. Invest. Dermatol. 106: 49, 1996.
19. Marikovsky, M., Breuing, K., Liu, P. Y., Eriksson, E., Higashiyama, S., Farber, P., Abraham, J., and Klagsbrun, M. Appearance of heparin-binding EGF-like growth factor in wound fluid as a response to injury. Proc. Natl. Acad. Sci USA 90: 3889, 1993.
20. Homma, T., Sakai, M., Cheng, H. F., Yasuda, T., Coffey, R. J., Jr., and Harris, R. C. Induction of heparin-binding epidernal growth factor-like growth factor mRNA in rat kidney after acute injury. J. Clin. Invest. 96: 1018, 1995.
21. de Boer, W. I., Rebel, J. M. J., Vermey, M., de Jong, A. A. W., and van der Kwast, T. H. Characterization of distinct functions for growth factors in murine transitional epithelial cells in primary organotypic culture. Exp. Cell Res. 214: 510, 1994.
22. Jorgensen, P. E., Hilchey, S. D., Nexo, E., Poulsen, S. S., and Quilly, C. P. Urinary epidermal growth factor is excreted from the rat isolated perfused kidney in the absence of plasma. J. Endocrinol. 139: 227, 1993.
23. Southgate, J., Hutton, A. R., Thomas, D. F. M., and Trejdosiewicz, L. K. Nornal human urothelial cells in vitro: proliferation and induction of stratification. Lab. Invest. 71: 583, 1994.
24. Chin, E. and Bondy, C. Insulin-like growth factor system gene expression in the human kidney. J. Clin. Endocrinol. Metab. 75: 962, 1992.
25. Jones, J. I. and Clemmons, D. R. Insulin-like growth factors and their binding proteins: biological actions. Endocrine Rev. 16: 3, 1995.
26. Freeman, M. R., Schneck, F. X., Soker, S., Raab, C., Tobin, M., Yoo, J., Klagsbrun, M., and Atala, A. Human urothelial cells secrete and are regulated by heparin-binding epidermal growth factor-like growth factor (HB-EGF). Proc. Am. Urol. Assoc. 153: 316A, 1995.
27. Tobin, M. S., Freeman, M. R., Schneck, F. X., Klagsbrun, M., and Atala, A. Growth factor biology of human urothelial cells grown under serum-free conditions. Proc. Am. Urol. Assoc. 153:406A, 1995.
28. Division of Kidney, Urologic, and Hematologic Diseases (DKUHD) of the National Institute of Diabetes and Digestive and Kidney Diseases (NIDDK). Diagnostic criteria for research studies (interstitial cystitis). Am. J. Kidney Dis. 13: 353, 1989.
29. Third International Symposium on Insulin-like Growth Factors. Valid measurements of total IGF concentrations in biological fluids. Endocrinology 136: 816, 1995.
30. Schirmeister, J., Willman, H., and Kiefer, H. Plasmakreatinin alf grober Indikator der Nierenfunktion. Dtsch. Med. Wschr. 89: 1018, 1964.
31. Shishido, Y., Sharma, K. D., Higashiyama, S., Klagsbrun, M., Mekada, E. Heparin-like molecules on the cell surface potentiate binding of diptheria toxin to the diphtheria toxin receptor/membrane-anchored heparin-binding epidernal growth factor-like growth factor. J. Biol. Chem. 270: 29578, 1995.

All references cited herein are incorporated by reference in their entirety.

The examples provided herein are for illustrative purposes only, and are in no way intended to limit the scope of the present invention. While the invention has been described in detail, and with reference to specific embodiments thereof, it will be apparent to one with ordinary skill in the art that various changes and modifications can be made therein without departing from the spirit and scope thereof.

What is claimed:

1. A method for diagnosing a condition associated with inhibited bladder epithelial cell proliferation comprising the steps of:

determining the level of epidermal growth factor in urine from the subject; and comparing said level with normal level, according to the following criterion:

increased level of epidermal growth factor, as compared to level of epidermal growth factor in a normal population, indicates the presence of the condition.

2. The method of claim 1 wherein the condition is interstitial cystitis.

3. The method of claim 1 wherein the subject presents with pain and/or urgency and/or frequency of urination.

4. The method of claim 1 wherein the subject presents with ulcers of the bladder mucosa and/or petechial hemorrhages of the bladder mucosa after hydrodistention of the bladder.

5. A method for diagnosing interstitial cystitis in a patient presenting interstitial cystitis symptom(s), comprising the steps of:

measuring epidermal growth factor level in urine from the patient; and comparing said epidermal growth factor level in urine from the patient with urine levels of epidermal growth factor in a normal asymptomatic population, to determine if said epidermal growth factor level in urine from the patient is elevated in relation to urine levels of epidermal growth factor in said normal asymptomatic population, whereby an elevated epidermal growth factor level in urine from the patient is supportive of a diagnosis of interstitial cystitis.

6. The method of claim 5, wherein said interstitial cystitis symptom(s) comprise one or more of the symptoms selected from the group consisting of: pain of urination; urgency of urination; frequency of urination; ulcers of bladder mucosa; and petechial hemorrhages of bladder mucosa.

7. The method of claim 5 wherein the subject presents with pain and/or urgency and/or frequency of urination.

8. The method of claim 5 wherein the subject presents with ulcers of the bladder mucosa and/or petechial hemorrhages of the bladder mucosa after hydrodistention of the bladder.

9. The method of claim 5, wherein said step of measuring epidermal growth factor level in urine from the patient comprises use of epidermal growth factor-binding antibodies.

10. The method of claim 5, wherein said step of measuring epidermal growth factor level in urine from the patient comprises use of a biological assay.

11. The method of claim 5, wherein said step of measuring epidermal growth factor level in urine from the patient comprises use of an immunoassay.

12. A diagnostic kit for diagnosing a condition associated with inhibited bladder epithelial cell proliferation, said diagnostic kit comprising:
   means for determining the level of epidermal growth factor in urine from the subject; and
   instructions for comparing said level with normal level, according to the following criterion:
   increased level of epidermal growth factor, as compared to level of epidermal growth factor in a normal population, indicates the presence of the condition.

13. The diagnostic kit of claim 12 wherein the condition is interstitial cystitis.

* * * * *